(12) United States Patent
Gausepohl

(10) Patent No.: US 7,481,980 B2
(45) Date of Patent: Jan. 27, 2009

(54) DEVICE FOR STAINING AND HYBRIDIZATION REACTIONS

(75) Inventor: Heinrich Gausepohl, Köln (DE)

(73) Assignee: Intavis Bioanalytical Instruments AG, Cologne (DE)

( * ) Notice: Subject to any disclaimer, the term of this patent is extended or adjusted under 35 U.S.C. 154(b) by 846 days.

(21) Appl. No.: 10/936,245

(22) Filed: Sep. 8, 2004

(65) Prior Publication Data
US 2006/0051253 A1    Mar. 9, 2006

(51) Int. Cl.
*B01L 9/00* (2006.01)

(52) U.S. Cl. .................................... 422/104
(58) Field of Classification Search .............. 422/104
See application file for complete search history.

(56) References Cited

U.S. PATENT DOCUMENTS

2002/0123064 A1* 9/2002 Sato et al. .................. 435/6

* cited by examiner

*Primary Examiner*—Walter D Griffin
*Assistant Examiner*—Bobby Ramdhanie
(74) *Attorney, Agent, or Firm*—Frommer Lawrence & Haug LLP; Ronald R. Santucci

(57) ABSTRACT

A device to perform complex protocols in immuno-cytochemistry and in situ hybridization on specimens attached to microscope sliders wherein such device encloses a biological material attached to a glass slide in such a way that a capillary gap is formed in combination with a cover plate equipped with spacers and allows individual treatment of each slide with reagents while also allowing automated liquid exchange with no cross contamination with the use of low reagent volume and the controlled evaporation during long incubations and elevated temperature as required for in situ hybridization in a simple and compact design for easy handling.

22 Claims, 3 Drawing Sheets

DEVICE FOR STAINING AND HYBRIDIZATION REACTIONS

SUMMARY

Figures 1A, 1B:
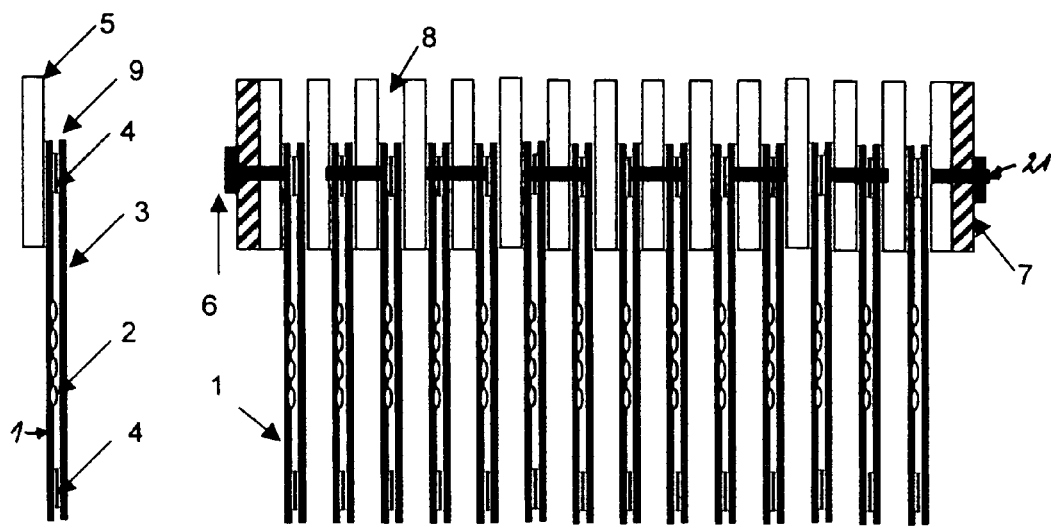

The invention describes a device to perform complex protocols in immuno-cytochemistry and in situ hybridization on specimens attached to microscope slides. Main purpose of the invention is to provide a device enabling automated performance of such protocols in a designated instrument. This is solved by clamping a slide with specimen against a cover slide in such a way that a small gap is formed between the two. Several pairs of such slides are held apart by sealing plates shaped in such a way as to form a reservoir above each pair of slides at the same time. Liquid filled into any of these reservoirs enters the gap between the slides from the top and is held there by capillary forces if the dimensions of the gap are selected appropriately. New liquid added will flow down and replace the liquid in the gap. Several such assemblies of slide, cover plate and spacer are held in a clamping mechanism. Each reservoir can be filled either manually or by a pipetting robot, or by any other liquid delivery mechanism.

For experiments involving in situ hybridization the clamping mechanism with one or more such assemblies is held in a moist chamber which can be heated. Evaporation via the open gaps at the side of the pairs of slides is such reduced to an acceptable level.

DESCRIPTION OF THE INVENTION

The analysis of gene expression patterns or of the spatial distribution of immunoreactive molecules is an established method in modern biology and medicine. While most of such analyses are carried out on tissue sections, a new area of application is gaining importance. Here the expression patterns in libraries of biological molecules attached to a planar carrier by mechanical or chemical means are analyzed. These libraries are also called "Biochips", micro arrays or DNA/protein/antibody chips, depending on the molecules attached. Protocols for hybridization on such libraries or tissue sections are labour intensive and require a series of incubations with different wash solutions and reagents. Some of these steps must be performed at a defined temperature and in many steps a contamination with ubiquitous enzymes must be prevented. The central step is an incubation over several hours with a sample of limited volume. The multitude of steps makes automation desirable. Devices for manual performance of hybridization are well-known and available from companies such as Sigma-Aldrich. Here a chamber is formed on the glass slide by means of a plastic cover slip and a silicone frame. Two openings allow addition and withdrawal of liquids. They are covered during hybridization and automated liquid exchange is not possible.

There are instruments on the market for simple staining reactions (DAKO, Denmark) as well as for more complex protocols (Biogenex, USA; Ventana, USA). All instruments have drawbacks if for each slide a specific sample with limited volume is available. Staining instruments as used for pathology are not usable for hybridization at elevated temperature as they work with open troughs. There are a few reports in the literature on manual procedures for hybridization as well as automated ones (Wilkinson, Oxford IRL Press 1982), but none of them has been commercialized successfully.

Instruments described in patents exhibit specific drawbacks which are overcome by the invention described in this application.

EP-A 0310399 (Shandon Ltd., UK) describes a holder made from polystyrene. As discussed in DE 199 41 905 this device can not be used for in situ hybridization at elevated temperature. DE 199 41 905 describes a similar device made from glass which requires a lot of space and a complicated clamping mechanism. Due to the very thick cover plate it also has a large thermal mass which takes long to heat and cool.

A device described in U.S. Pat. No. 775,864 is used by DAKO for tissue staining. Here liquids are drawn upwards into the capillary gap between two adjacent slides and removed again by touching a drain wick. The procedure is slow and not usable for in situ hybridization. The gap can not easily be washed thoroughly.

U.S. Pat. No. 6,183,693 describes a heatable device for in situ hybridization treating the samples on horizontal, open slides in a fashion similar to that described in U.S. Pat. No. 5,425,918. Here large volumes of reagents are needed and evaporation is difficult to control.

An early application of capillary gaps in tissue staining is described in U.S. Pat. No. 840,651 and GB 2008 270. Here the liquid is poured onto the sides of a plurality of slides which are held at a distance to form capillary gaps. All gaps are treated with liquid simultaneously and the liquid can drain along the edges of the slides.

The purpose of this invention is to provide a device fulfilling the following requirements:
- enclose the biological material attached to a glass slide in such a way that a capillary gap is formed in combination with a cover plate equipped with spacers
- allow individual treatment of each slide with reagents
- allow automated liquid exchange with no cross contamination
- use low reagent volume
- control evaporation during long incubations and elevated temperature as required for in situ hybridization
- provide a simple and compact design for easy handling According to one embodiment of the invention, an assembly of construction elements is provided comprising two or more sets of construction elements, wherein each set comprises
- a slide 1,
- a cover plate 3,
- one ore more spacer elements 4 adapted to keep the slide 1 and the cover plate 3 parallel to each other at a distance corresponding to a capillary gap 9,
- a sealing element 5 for separating each pair of slide 1 and cover plate 3 from a neighbouring pair and forming a reservoir above the capillary gap in cooperation with the neighbouring sealing element and
- a compression device for compressing the sets together and holding the slides 1 with their cover plates 3 in an essentially vertical position.

The slide 1 and the cover plate 3 of the assembly according to the invention may have the same length and width and are preferably microscope slides.

Further, the sealing elements of the assembly according to the invention may consist of a resilient material selected from the group of silicone, rubber, an inert elastomer or a material coated with silicone, rubber or an inert elastomer.

Further, each sealing element 5 of the assembly according to the invention may be provided as a channel which can be closed by a neighbouring sealing element 5 for fittingly receiving a pair of slide 1 and cover plate 3.

Further, each sealing element 5 of the assembly according to the invention may have a cross section of a wide U or of a double T.

Further, according to the invention, neighbouring sealing elements 5 each may form a reservoir above the top edges of the pairs of slide 1 and cover plate 3 for loading the capillary gaps 9 with liquid.

Further, according to the invention, two sealing elements 5 spaced apart from each other by more than one pair of slide 1 and cover plate 3, each may form a reservoir (secondary reservoir) 19, 20 across the pairs of slide 1 and cover plate 3 provided between said sealing elements 5.

Further, the capillary gaps 9 of the assembly according to the invention may open not only at the upper and bottom narrow sides but also at most of both longitudinal sides.

Further, the spacer elements 4 of the assembly according to the invention may be solid stripes 12, 13, dots, triangles 11 or rectangles.

Further, the spacer elements 4 of the assembly according to the invention may be provided at the corners or alongside the lateral edges or additionally at the center line of each slide 1 and its related cover plate 3 in the area of compression by the sealing elements.

Further, the spacer elements 4 of the assembly according to the invention may be carried on the slides 1 or the cover plates 3 or on both.

Further, the spacer elements of the assembly according to the invention may be glued, polymerized or printed onto the slides 1 or cover plates 3 or on both.

Further, the sets of structural elements of the assembly according to the invention may be held together by a clamping device 6 which comprises clamp plates 7 on both sides of a stack of said sets.

Further, the sealing elements 5 of the assembly according to the invention may be provided with through holes 10 for receiving a rod or bolt 21 arrested by means of the clamp plates 7.

The assembly according to the invention may be provided for treatment of biological samples with liquids wherein the biological samples are provided on the slides.

Another embodiment of the invention concerns a cover plate especially for an assembly or a device according to the invention, wherein the cover plate 3 is provided with spacer elements 5.

Still another embodiment of the invention concerns a sealing element especially for an assembly or a device according to the invention, wherein the sealing element is provided as part of a reservoir above the top edges of a pair of slide 1 and cover plate 3 for loading a capillary gap 9 between said slide 1 and said cover plate 3 with liquid.

Still another embodiment of the invitation concerns a trough as receptacle for one or more assemblies according to the invention, wherein the trough 14 is covered by a lid 15 which is provided with holes in alignment with each capillary gap 9 formed by a pair of slide 1 and cover plate 3.

The trough 14 according to the invention may be heatable and provides a moist environment for the said assemblies during treatment with liquids.

Still another embodiment of the invention concerns a procedure for treatment of biological samples attached to a slide 1 in which a cover plate 3 is posed across the slide 1 with a capillary gap 9 formed between them and which is held in a vertical position and in which liquids are delivered on the top edge of the gap 9 and exit at the bottom.

In the procedure according to the invention, one or more assemblies of slide 1, cover plate 3 and sealing element 5 according to the invention may be treated with liquid common to all assemblies or specific to individual assemblies.

Finally, in the procedure according to the invention, one ore more assemblies of slide 1, cover plate 3 and sealing element 5 according to the invention may be kept in a moist, temperature controlled sealed trough during treatment with liquids.

According to another embodiment of the invention an assembly of construction elements is provided comprising one set of construction elements, wherein the set comprises a slide (1), a cover plate (3), one ore more spacer elements (4) adapted to keep the slide (1) and the cover plate (3) parallel to each other at a distance corresponding to a capillary gap (9).

The assembly of construction elements according to the invention may comprise two or more sets of construction elements, wherein each set comprises a slide (1), a cover plate (3), one ore more spacer elements (4) adapted to keep the slide (1) and the cover plate (3) parallel to each other at a distance corresponding to a capillary gap (9), a sealing element (5) for separating each pair of slide (1) and cover plate (3) from a neighbouring pair of slide (1) and cover plate (3) and a compression device for compressing the sets together and holding the slides (1) with their cover plates (3) in an essentially vertical position.

Further, the slide (1) and the cover plate (3) of the assembly according to the invention may have the same length and width and are preferably microscope slides.

Further, the invention concerns a compression device comprising one set of construction elements, wherein the set comprises a slide (1), a cover plate (3), one ore more spacer elements (4) adapted to keep the slide (1) and the cover plate (3) parallel to each other at a distance corresponding to a capillary gap (9).

As regards the compression device according to the invention comprising two or more sets of structural elements, each set may comprise a slide (1), a cover plate (3), one ore more spacer elements (4) adapted to keep the slide (1) and the cover plate (3) parallel to each other at a distance corresponding to a capillary gap (9), and a sealing element (5) for separating each pair of slide (1) and cover plate (3) from a neighbouring pair of slide (1) and cover plate (3), wherein the compression device compresses the sets together and holds the slides (1) with their cover plates (3) in an essentially vertical position.

Further, the slide (1) and the cover plate (3) of the compression device according to the invention may have the same length and width and are preferably microscope slides.

Further, the sealing elements of the compression device according to the invention may consist of a resilient material selected from the group of silicone, rubber, an inert elastomer or a material coated with silicone, rubber or an inert elastomer.

Further, each sealing element (5) of the compression device according to the invention may be provided as a channel and can be closed by a neighbouring sealing element (5) for fittingly receiving a pair of slide (1) and cover plate (3).

Further, each sealing element (5) of the compression device according to the invention may have a cross section of a U or of a double T.

Further, neighbouring sealing elements (5) of the compression device according to the invention may each form a reservoir above the top edges of the pairs of slide (1) and cover plate (3) for loading the capillary gaps (9) with liquid.

Further, two sealing element (5) of the compression device according to the invention may be spaced apart from each other by more than one pair of slide (1) and cover plate (3), each form a reservoir (secondary reservoir) (19, 20) across the pairs of slide (1) and cover plate (3) provided between said sealing element (5).

Further, the capillary gaps (9) of the compression device according to the invention may be open not only at the upper and bottom narrow sides but also at both longitudinal sides.

Further, the spacer elements (4) of the compression device according to the invention may be solid stripes (12, 13), dots, triangles (11) or rectangles.

Further, the spacer elements (4) of the compression device according to the invention may be provided at the corners or alongside the lateral edges or additionally at the center line of each slide (1) and its related cover plate (3).

Further, the spacer elements (4) of the compression device according to the invention may be carried on the slides (1) or the cover plates (3) or on both.

Further, the spacer elements of the compression device according to the invention may be glued, polymerized or printed onto the slides (1) or cover plates (3) or on both.

Further, the sets of structural elements of the compression device according to the invention may be hold together by a clamping device (6).

Further, the sets of structural elements of the compression device according to the invention may be hold together by a clamping device (6) which comprises clamp plates (7) on both sides of a stuck of said sets.

Further, the sealing elements (5) of the compression device according to the invention may be provided with through holes (10) for receiving a rod or bolt (21) arrested by means of the clamp plates (7).

Further, the compression device according to the invention may be provided for treatment of biological samples with liquids.

Further, the invention concerns a cover plate especially for an assembly or a device according to the invention, wherein the cover plate (3) is provided with spacer elements (5).

Further, the spacer elements (4) of the cover plate (3) according to the invention may be provided at the corners or alongside the lateral edges or additionally at the center line of said cover plate (3).

Further, the spacer elements (4) of the cover plate according to the invention may be solid stripes (12, 13), dots, triangles (11) or rectangles.

Further, the spacer elements of the cover plate according to the invention may be glued, polymerized or printed onto the cover plate (3).

Further, the invention concerns a sealing element especially for an assembly or a device according to the invention, wherein the sealing element consists of a resilient material selected from the group of silicone, rubber, an inert elastomer or a material coated with silicone, rubber or an inert elastomer.

Further, the sealing element (5) according to the invention may be provided as a channel which can be closed by another sealing element (5) for fittingly receiving a pair of slide (1) and cover plate (3).

Further, the sealing element (5) according to the invention may have a cross section of a U or of a double T.

Further, the sealing element according to the invention may be provided as part of a reservoir above the top edges of a pair of slide (1) and cover plate (3) for loading a capillary gap (9) between said slide (1) and said cover plate (3) with liquid.

Further, the invention concerns a trough as receptacle (14) for one or more compression devices according to the invention.

Further, the trough (14) according to the invention may be sealable and heatable.

Further, the trough (14) according to the invention may be provided with an overflow outlet (17) or a bottom outlet or both.

Further, the trough (14) according to the invention may be covered by a lid (15) which is provided with sealable holes in alignment with each capillary gap (9) formed by a pair of slide (1) and cover plate (3).

Further, the lids (15) of the trough according to the invention may be formed by sealings which can be penetrated by a pipetting needle.

Further, the trough (14) according to the invention may be provided with supports for holding one or more compression devices.

Further, the invention concerns a process for treatment of biological samples attached to a slide (1) in which a cover plate (3) is posed across the slide (1) with a capillary gap (9) formed between them and which is held in a vertical position and in which liquids are delivered on the top edge of the gap (9) and exit at the bottom.

Further, according to the process according to the invention, one ore more assemblies of slide (1), cover plate (3) and sealing element (5) according to the invention can be treated with liquid common to all assemblies or specific to individual assemblies.

Finally, according to the process according to the invention, one or more assemblies of slide (1), cover plate (3) and sealing element (5) may be kept in a moist, temperature controlled sealed trough during treatment with liquids.

In other words the task is solved by a device described in the patent and its claims and shown in FIGS. 1 to 4. The device described allows automated performance of protocols for in situ hybridization in a dedicated instrument. A significant reduction of the work load is achieved and experiments are made more reproducible.

FIGS. 1a&b show the cross section, and

Figures 2A, 2B:
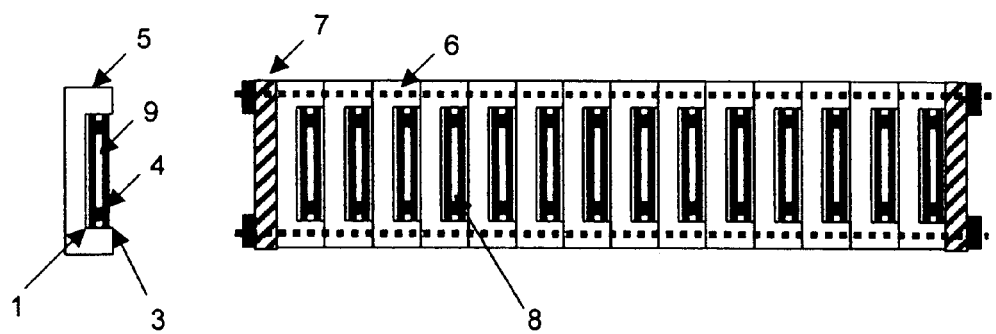

FIGS. 2a&b show the top view on the device

Figure 3A:
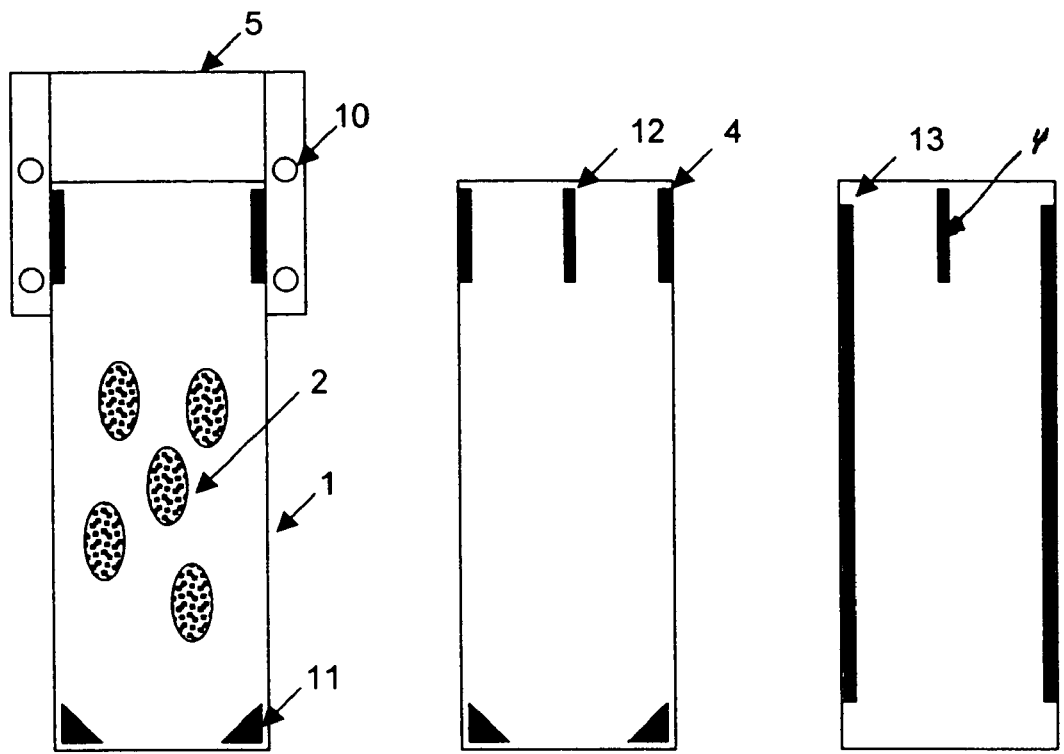

FIGS. 3a-c show a possible arrangement of specimens on the slide

Figure 4:
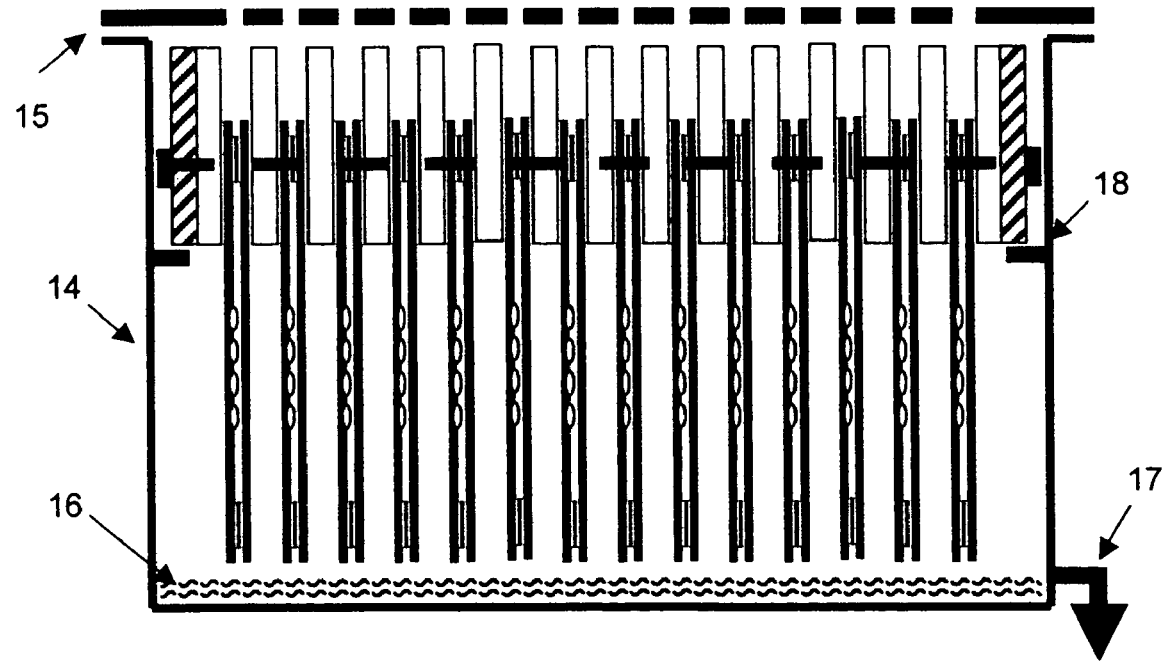

FIG. 4 shows a plurality of slides in a wet chamber

FIGS. 5a&b show other embodiments compared to those of FIGS. 3 and 1.

A plurality of slides 1 with samples of a biological material 2, cover plates 3 and spacers 4 with sealing plates 5 is arranged in a parallel, vertical fashion, stacked and compressed with the aid of a clamping mechanism 6 and clamping plates 7. In this arrangement individual reservoirs 8 are formed above each pair of slide 1 and cover plate 3 in conjunction with the compressed sealing plates 5. Spacers 4 at top and bottom of the cover plate 3 ensure parallel orientation of slide 1 and cover plate 3. The capillary gap formed 9 is open at all sides except where the spacers 4 are located (see FIG. 3c).

Liquid poured onto the top edges of a pair of slide 1 and cover plate 3 flows into the capillary gap 9 by gravity and exits at the bottom edge. If the gap 9 has a suitable width of less than 0.2 mm it remains filled by capillary forces. If a second liquid is added, it replaces the first one with a front well defined because of the small gap distance. Liquids can be replaced very effectively with a volume of 1.5 to 2 time the gap volume.

The sealing plates 5 are profiled to accept a pair of slide 1 and cover plate 3 each, as shown in FIG. 2. If the sealing plates 5 are made from an elastic material such as silicone or rubber they seal against each other under compression and form reservoirs 8. The reservoirs 8 formed by the combination of sealing plates 5, slides 1 and cover plates 3 allow treatment of each sample with an individual probe. The reservoir 8 can be dimensioned to hold a multiple of the gap volume. In this way, complete exchange of liquids is ensured with just one filling of the reservoir 8. Commercial slides 1 may vary slightly in their dimensions and the sealing between the sealing plates 5, slide 1 and cover plate 3 may occasionally be insufficient. The device described is tolerant towards such inaccuracies. Leakages are confined to individual pairs of slide 1 and cover plate 3 with no cross contamination of other slides 1. Liquid escaping at the side edges is drawn back into the capillary gap 9 and exits at the bottom without contacting other slides 1.

Several sets of sealing plates 5, slides 1 and cover plates 3 are compressed by a clamping device 6. The clamping device consists of a pair of threaded bolts 21 and stainless steel clamping plates 7 or a more sophisticated arrangement providing the same compression.

Typical protocols of immunostaining and in situ hybridization are will described in literature (e.g. Wilkinson, in situ Hybridization, IRL press) and in the patents cited above. All protocols comprise a serial incubation of biological samples with a number of liquids of different composition and viscosity. Incubations may have to be performed also at elevated or reduced temperature. Occasionally, air bubbles are generated by degassing of liquids in the gap 9. It is advantageous to degas the liquids before use, but bubbles are also washed out of the gap 9 by subsequent washing steps.

The device described allows to arrange a plurality of slides 1 in a confined space. The following description depicts an example only, without prejudice or constriction of the patent claim to these dimensions. A typical arrangement has a space requirement of 5 mm per unit, including a 3 mm gap between pairs of slides. At a gap width of 0.075 mm the gap volume is 140 µl using commercial slides of 25×75 mm. An ideal reservoir volume is 500 to 600 µl. Cover plates 3 are preferentially made from microscope slides matching those for the sample, onto which spacer elements 4 have been applied. The spacer elements 4 can be stripes as shown in FIG. 3 (4, 12, 13) or other geometric elements. A spacer element 4 in the top center 12 prevents deformation of slide 1 and cover plate 3 by the elastic sealing plates 5. Long stripes along the edges hold the gap 9 at a defined distance and reduce the evaporation along otherwise open edges.

The spacer elements 4 can be made from inert adhesive film, plastic polymerized on the plates, or paint printed on to the cover plates 3.

Experiments of in situ hybridization require incubation of the samples at elevated temperature for an extended time, e.g. 16 h at 60° C. Because of the open edges of each pair of slide 1 and cover plate 3 the device must be kept in a wet chamber with saturated atmosphere to prevent evaporation of the liquid in the gap 9. Such a chamber 14 is depicted in FIG. 4. Here the compact arrangement of the elements is advantageous, as a small chamber 14 is readily saturated with vapour. The drain 17 is arranged in such a way, that a reservoir of liquid 16 remains in the chamber 14 at all times. Heating elements (not shown) are arranged on the bottom and sides. Preferentially, the bulk of heating energy is provided via the bottom to generate vapour for saturation of the atmosphere quickly.

Delivery of liquids to the individual reservoirs 8 is accomplished by the needle of a pipetting robot via holes in the wet chamber cover 15. The liquid is either added drop wise to the upper edges of slide 1 and cover plate 3 or deposited in the reservoirs 8 formed by sealing plates 5, slide 1 and cover plate 3.

For cooling the heating elements are switched off and the warm liquid in the wet chamber 14 is replaced by cold liquid. In addition, the chamber 14 may be actively cooled, e.g. by Peltier elements (not shown). Slides 1 and cover plates 3 may additionally be cooled by delivery of cold liquid to the capillary gaps 9. This may be required to prevent evaporation from the capillary gap 9 when the dew point in the chamber 14 drops suddenly. For rapid cooling it is also possible to flood the entire chamber 14 with wash buffer (not shown). Cross contamination will be low as the reagents left in the chamber 14 are readily diluted and diffusion into the capillary gaps 9 is very slow. Flooding of the chamber 14 can therefore not replace the wash steps in which liquid is added to the reservoirs 8 on top of the slides.

Figure 5:
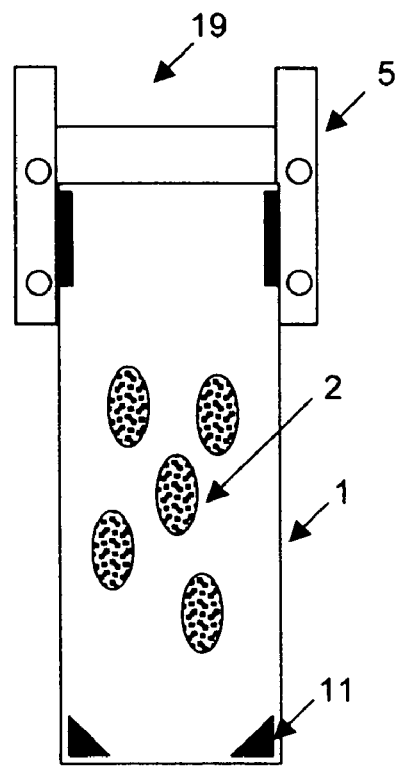
Figure 5:
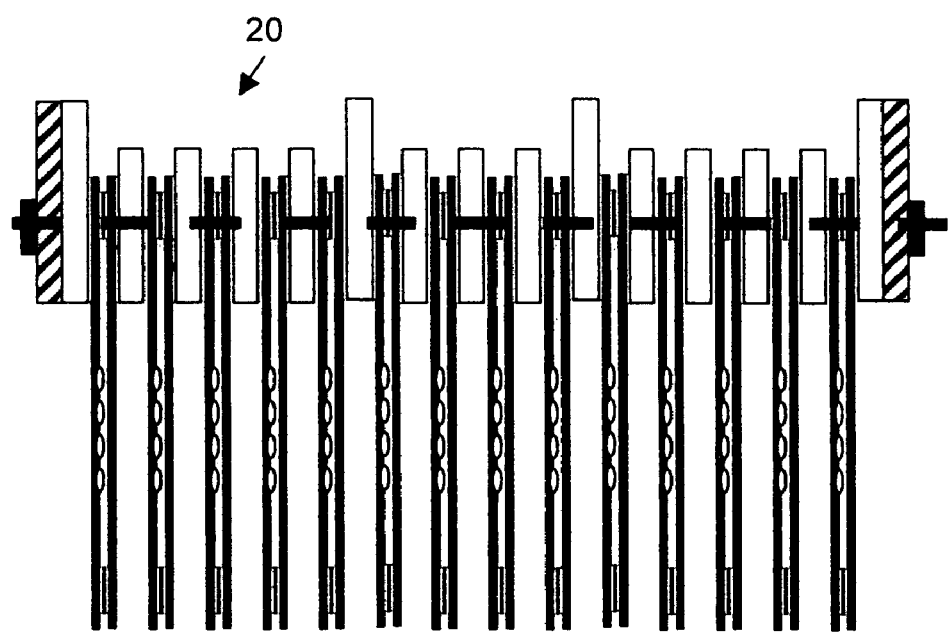

According to another embodiment of the device as shown in FIG. 5b some of the sealing plates 5 have a geometry, which leads to formation of secondary reservoirs 20 across two or more pairs of slide 1 and cover 3. The respective geometry is shown in FIG. 5. In this arrangement the liquid for washing of more than one unit can be applied at one time, speeding up the process. Small residual individual reservoirs 8 should be retained to allow individual treatment with specific probes for each slide 1.

Device for Staining and Hybridization Reactions

Legend for Figures
  1: Microscope slide
  2: Sample of biological material
  3: Cover plate
  4: Spacer
  5: Sealing plate
  6: Clamping device
  7: Clamp plate
  8: Reservoir
  9: Capillary gap
  10: Hole for clamping device
  11: Spacer, alternative shape
  12: Spacer
  13: Abstandshalter, long version
  14: Wet chamber
  15: Lid
  16: Liquid residue
  17: Drain
  18: Holder
  19: Reservoir gap
  20: Secondary reservoir

The invention claimed is:
1. An assembly of construction elements for staining and hybridization reactions comprising two or more sets of construction elements, wherein each set comprises
  a slide (1),
  a cover plate (3),
  one or more spacer elements (4) adapted to keep the slide (1) and the cover plate (3) parallel to each other at a distance corresponding to a capillary gap (9),
  a sealing element (5) for separating each pair of slide (1) and cover plate (3) from a neighbouring pair and forming a reservoir above the capillary gap in cooperation with the neighbouring sealing element and
  a compression device for compressing the sets together and holding the slides (1) with their cover plates (3) in an essentially vertical position.

2. An assembly according to claim 1, wherein the slide (1) and the cover plate (3) have the same length and width and are preferably microscope slides.

3. An assembly according to claim 1, wherein the sealing elements consist of a resilient material selected from the group of silicone, rubber, an inert elastomer or a material coated with silicone, rubber or an inert elastomer.

4. An assembly according to claim 1, wherein each sealing element (5) is provided as a channel which can be closed by a neighbouring sealing element (5) for fittingly receiving a pair of slide (1) and cover plate (3).

5. An assembly according to claim 1, wherein each sealing element (5) has a cross section of a wide U or of a double T.

6. An assembly according to claim 1, wherein neighbouring sealing elements (5) each form a reservoir above the top edges of the pairs of slide (1) and cover plate (3) for loading the capillary gaps (9) with liquid.

7. An assembly according to claim 1, wherein two sealing elements (5) spaced apart from each other by more than one pair of slide (1) and cover plate (3), each form a reservoir (secondary reservoir) (19, 20) across the pairs of slide (1) and cover plate (3) provided between said sealing elements (5).

8. An assembly according to claim 1, wherein the capillary gaps (9) are open not only at the upper and bottom narrow sides but also at most of both longitudinal sides.

9. An assembly according to claim 1, wherein the spacer elements (4) are solid stripes (12, 13), dots, triangles (11) or rectangles.

10. An assembly according to claim 1, wherein the spacer elements (4) are provided at the corners or alongside the lateral edges or additionally at the center line of each slide (1) and its related cover plate (3) in the area of compression by the sealing elements.

11. An assembly according to claim 1, wherein the spacer elements (4) are carried on the slides (1) or the cover plates (3) or on both.

12. An assembly according to claim 1, wherein the spacer elements are glued, polymerized or printed onto the slides (1) or cover plates (3) or on both.

13. An assembly according to claim 1, wherein the sets of structural elements are held together by a clamping device (6) which comprises clamp plates (7) on both sides of a stack of said sets.

14. An assembly according to claim 1, wherein the sealing elements (5) are provided with through holes (10) for receiving a rod or bolt (21) arrested by means of the clamp plates (7).

15. An assembly according to claim 1 for treatment of biological samples with liquids wherein the biological samples are provided on the slides.

16. A cover plate especially for an assembly or a device according to claim 1, wherein the cover plate (3) is provided with spacer elements (5).

17. A sealing element especially for an assembly or a device according to claim 1, wherein the sealing element is provided as part of a reservoir above the top edges of a pair of slide (1) and cover plate (3) for loading a capillary gap (9) between said slide (1) and said cover plate (3) with liquid.

18. A trough as receptacle for one or more assemblies according to claim 1, wherein the trough (14) is covered by a lid (15) which is provided with holes in alignment with each capillary gap (9) formed by a pair of slide (1) and cover plate (3).

19. A trough according to claim 18, wherein the trough (14) is heatable and provides a moist environment for the said assemblies during treatment with liquids.

20. A procedure for treatment of biological samples attached to a slide (1) in which a cover plate (3) is posed across the slide (1) with a capillary gap (9) formed between them and which is held in a vertical position and in which liquids are delivered on the top edge of the gap (9) and exit at the bottom.

21. A procedure according to claim 20, in which one or more assemblies of slide (1), cover plate (3) and sealing element (5) according to one or more of the claims 1 to 19 are treated with liquid common to all assemblies or specific to individual assemblies.

22. A procedure according to claim 20 in which one or more assemblies of slide (1), cover plate (3) and sealing element (5) are kept in a moist, temperature controlled sealed trough during treatment with liquids.

* * * * *